(12) United States Patent
Tun et al.

(10) Patent No.: US 9,370,329 B2
(45) Date of Patent: Jun. 21, 2016

(54) MAP AND ABLATE CLOSED-LOOP COOLED ABLATION CATHETER

(71) Applicant: Boston Scientific Scimed, Inc., Maple Grove, MN (US)

(72) Inventors: Zaya Tun, Livermore, CA (US); Isaac J. Kim, San Jose, CA (US); Josef V. Koblish, Sunnyvale, CA (US); Minhchau N. Cao, San Jose, CA (US); Steve Ha, Hayward, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 69 days.

(21) Appl. No.: 14/029,533

(22) Filed: Sep. 17, 2013

(65) Prior Publication Data

US 2014/0081111 A1    Mar. 20, 2014

Related U.S. Application Data

(60) Provisional application No. 61/702,626, filed on Sep. 18, 2012.

(51) Int. Cl.
*A61B 5/042*    (2006.01)
*A61B 18/14*   (2006.01)
(Continued)

(52) U.S. Cl.
CPC ......... *A61B 5/6853* (2013.01); *A61B 5/04012* (2013.01); *A61B 5/0422* (2013.01); *A61B 5/4836* (2013.01); *A61B 18/1206* (2013.01); *A61B 18/1492* (2013.01); *A61B 18/18* (2013.01); *A61M 5/00* (2013.01); *A61B 2017/00044* (2013.01);
(Continued)

(58) Field of Classification Search
CPC ............... A61B 5/0422; A61B 2018/00577; A61B 2018/1405; A61B 18/1492
USPC .............................. 600/374; 606/41
See application file for complete search history.

(56) References Cited

U.S. PATENT DOCUMENTS 4,732,149 A    3/1988 Sutter
4,763,660 A    8/1988 Kroll et al.
(Continued)

FOREIGN PATENT DOCUMENTS

CA    2682055 A1    10/2008
CN    1455655 A     11/2003
(Continued)

OTHER PUBLICATIONS

Goldberg, S. Nahum et al., "Variables Affecting Proper System Grounding for Radiofrequency Ablation in an Animal Model", JVIR, vol. 11, No. 8, Sep. 2000, pp. 1069-1075.
(Continued)

*Primary Examiner* — Lee S Cohen
(74) *Attorney, Agent, or Firm* — Faegre Baker Daniels LLP

(57) ABSTRACT

A system for performing mapping and ablation functions includes a catheter sized and shaped for vascular access. The catheter includes an elongate body extending between a proximal end and a distal end. A tip section positioned at the distal end of the catheter body and includes a proximal portion and a distal portion. One or more electrode structures are formed on an exterior surface of the tip section. The one or more electrode structures each includes a mapping electrode at the distal portion of the tip section and a contact pad electrically coupled to the mapping electrode.

18 Claims, 6 Drawing Sheets

(51) Int. Cl.
    *A61B 5/00*         (2006.01)
    *A61B 18/18*      (2006.01)
    *A61M 5/00*       (2006.01)
    *A61B 18/12*      (2006.01)
    *A61B 5/04*         (2006.01)
    *A61B 17/00*      (2006.01)
    *A61B 18/00*      (2006.01)

(52) U.S. Cl.
    CPC ............... *A61B 2018/00023* (2013.01); *A61B 2018/00136* (2013.01); *A61B 2018/00791* (2013.01); *A61B 2018/00839* (2013.01)

(56) References Cited

U.S. PATENT DOCUMENTS

| | | |
|---|---|---|
| 5,217,460 A | 6/1993 | Knoepfler |
| 5,238,004 A | 8/1993 | Sahatjian et al. |
| 5,254,088 A | 10/1993 | Lundquist et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,383,874 A | 1/1995 | Jackson et al. |
| 5,385,146 A | 1/1995 | Goldreyer |
| 5,391,199 A | 2/1995 | Ben-Haim |
| 5,398,683 A | 3/1995 | Edwards et al. |
| 5,423,811 A | 6/1995 | Imran et al. |
| 5,447,529 A | 9/1995 | Marchlinski et al. |
| 5,462,521 A | 10/1995 | Brucker et al. |
| 5,482,054 A | 1/1996 | Slater et al. |
| 5,500,012 A | 3/1996 | Brucker et al. |
| 5,573,535 A | 11/1996 | Viklund |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,800,482 A | 9/1998 | Pomeranz et al. |
| 5,820,568 A | 10/1998 | Willis |
| 5,830,213 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,913,856 A | 6/1999 | Chia et al. |
| 5,916,213 A | 6/1999 | Haissaguerre et al. |
| 6,027,500 A | 2/2000 | Buckles et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,083,222 A | 7/2000 | Klein et al. |
| 6,099,524 A | 8/2000 | Lipson et al. |
| 6,116,027 A | 9/2000 | Smith et al. |
| 6,120,476 A | 9/2000 | Fung et al. |
| 6,171,305 B1 | 1/2001 | Sherman |
| 6,200,314 B1 | 3/2001 | Sherman |
| 6,216,027 B1 | 4/2001 | Willis et al. |
| 6,233,491 B1 | 5/2001 | Kordis et al. |
| 6,270,493 B1 | 8/2001 | Lalonde et al. |
| 6,290,697 B1 | 9/2001 | Tu et al. |
| 6,400,981 B1 | 6/2002 | Govari |
| 6,475,213 B1 | 11/2002 | Whayne et al. |
| 6,488,678 B2 | 12/2002 | Sherman |
| 6,491,710 B2 | 12/2002 | Satake |
| 6,508,803 B1 | 1/2003 | Horikawa et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,547,788 B1 | 4/2003 | Maguire et al. |
| 6,575,966 B2 | 6/2003 | Lane et al. |
| 6,579,278 B1 | 6/2003 | Bencini |
| 6,602,242 B1 | 8/2003 | Fung et al. |
| 6,640,120 B1 | 10/2003 | Swanson et al. |
| 6,647,281 B2 | 11/2003 | Morency |
| 6,656,174 B1 | 12/2003 | Hegde et al. |
| 6,666,862 B2 | 12/2003 | Jain et al. |
| 6,719,756 B1 | 4/2004 | Muntermann |
| 6,735,465 B2 | 5/2004 | Panescu |
| 6,796,979 B2 | 9/2004 | Lentz |
| 6,796,980 B2 | 9/2004 | Hall |
| 6,811,550 B2 | 11/2004 | Holland et al. |
| 6,837,884 B2 | 1/2005 | Woloszko |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,932,811 B2 | 8/2005 | Hooven et al. |
| 6,950,689 B1 | 9/2005 | Willis et al. |
| 6,952,615 B2 | 10/2005 | Satake |
| 7,047,068 B2 | 5/2006 | Haissaguerre |
| 7,097,643 B2 | 8/2006 | Cornelius et al. |
| 7,112,198 B2 | 9/2006 | Satake |
| 7,247,155 B2 | 7/2007 | Hoey et al. |
| 7,347,857 B2 | 3/2008 | Anderson et al. |
| 7,438,714 B2 | 10/2008 | Phan |
| 7,519,410 B2 | 4/2009 | Taimisto et al. |
| 7,569,052 B2 | 8/2009 | Phan et al. |
| 7,736,362 B2 | 6/2010 | Eberl et al. |
| 7,740,629 B2 | 6/2010 | Anderson et al. |
| 7,799,025 B2 | 9/2010 | Wellman |
| 7,819,863 B2 | 10/2010 | Eggers et al. |
| 8,128,617 B2 | 3/2012 | Bencini et al. |
| 8,414,579 B2 | 4/2013 | Kim et al. |
| 8,579,889 B2 | 11/2013 | Bencini |
| 8,657,814 B2 | 2/2014 | Werneth et al. |
| 8,740,900 B2 * | 6/2014 | Kim et al. ................ 606/46 |
| 8,894,643 B2 * | 11/2014 | Watson et al. ........ A61B 1/0008 606/41 |
| 9,125,668 B2 | 9/2015 | Subramaniam et al. |
| 9,211,156 B2 | 12/2015 | Kim et al. |
| 2001/0029371 A1 | 10/2001 | Kordis |
| 2002/0087208 A1 | 7/2002 | Koblish et al. |
| 2003/0088240 A1 | 5/2003 | Saadat |
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0215186 A1 | 10/2004 | Cornelius et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2006/0089634 A1 | 4/2006 | Anderson et al. |
| 2006/0161146 A1 | 7/2006 | Cornelius et al. |
| 2006/0247607 A1 | 11/2006 | Cornelius et al. |
| 2006/0253116 A1 | 11/2006 | Avitall et al. |
| 2007/0049925 A1 | 3/2007 | Phan et al. |
| 2007/0270794 A1 | 11/2007 | Anderson et al. |
| 2008/0015568 A1 | 1/2008 | Paul et al. |
| 2008/0058836 A1 | 3/2008 | Moll et al. |
| 2008/0086073 A1 | 4/2008 | McDaniel |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0195089 A1 | 8/2008 | Thiagalingam et al. |
| 2008/0243214 A1 | 10/2008 | Koblish |
| 2008/0281322 A1 | 11/2008 | Sherman et al. |
| 2008/0300454 A1 | 12/2008 | Goto |
| 2008/0312713 A1 | 12/2008 | Wilfley et al. |
| 2009/0048591 A1 | 2/2009 | Ibrahim et al. |
| 2009/0062790 A1 | 3/2009 | Malchano et al. |
| 2009/0062795 A1 | 3/2009 | Vakharia et al. |
| 2009/0093810 A1 | 4/2009 | Subramaniam et al. |
| 2009/0093811 A1 | 4/2009 | Koblish et al. |
| 2009/0131932 A1 | 5/2009 | Vakharia et al. |
| 2009/0163904 A1 | 6/2009 | Miller et al. |
| 2009/0182316 A1 | 7/2009 | Bencini |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0299355 A1 | 12/2009 | Bencini et al. |

(56) References Cited

U.S. PATENT DOCUMENTS

| | | |
|---|---|---|
| 2010/0010487 A1 | 1/2010 | Phan et al. |
| 2010/0094274 A1 | 4/2010 | Narayan et al. |
| 2010/0106155 A1 | 4/2010 | Anderson et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168831 A1 | 7/2010 | Korivi et al. |
| 2010/0331658 A1 | 12/2010 | Kim et al. |
| 2011/0028820 A1 | 2/2011 | Lau et al. |
| 2011/0112569 A1 | 5/2011 | Friedman et al. |
| 2011/0125143 A1 | 5/2011 | Gross et al. |
| 2012/0101398 A1 | 4/2012 | Ramanathan et al. |
| 2012/0330304 A1 | 12/2012 | Vegesna et al. |
| 2013/0172715 A1 | 7/2013 | Just et al. |
| 2013/0190747 A1 | 7/2013 | Koblish et al. |
| 2013/0274582 A1 | 10/2013 | Afonso et al. |
| 2014/0012251 A1 | 1/2014 | Himmelstein et al. |
| 2014/0058375 A1 | 2/2014 | Koblish |
| 2014/0073893 A1 | 3/2014 | Bencini |
| 2014/0081112 A1 | 3/2014 | Kim et al. |
| 2014/0107453 A1 | 4/2014 | Maskara et al. |
| 2014/0107636 A1 | 4/2014 | Bencini |
| 2015/0011995 A1 | 1/2015 | Avitall et al. |
| 2015/0133914 A1 | 5/2015 | Koblish |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374436 A1 | 12/2015 | Subramaniam et al. |

FOREIGN PATENT DOCUMENTS

| | | |
|---|---|---|
| CN | 104640513 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 2136702 B1 | 7/2015 |
| JP | 200083918 A | 3/2000 |
| JP | 2009518150 A | 5/2009 |
| JP | 2010522623 A | 7/2010 |
| JP | 5336465 B2 | 11/2013 |
| JP | 2014012174 A | 1/2014 |
| KR | 20100021401 A | 2/2010 |
| KR | 101490374 B1 | 2/2015 |
| WO | WO9221278 A1 | 12/1992 |
| WO | WO9413358 A1 | 6/1994 |
| WO | WO9725916 A1 | 7/1997 |
| WO | WO9725917 A1 | 7/1997 |
| WO | WO9736541 A1 | 10/1997 |
| WO | WO9858681 A2 | 12/1998 |
| WO | WO9927862 A1 | 6/1999 |
| WO | WO0029062 A2 | 5/2000 |
| WO | WO2007079278 A1 | 7/2001 |
| WO | WO0158372 A1 | 8/2001 |
| WO | WO0164145 A1 | 9/2001 |
| WO | WO0205868 A2 | 1/2002 |
| WO | WO0209599 A2 | 2/2002 |
| WO | WO0219934 A1 | 3/2002 |
| WO | WO0247569 A1 | 6/2002 |
| WO | WO02102234 A2 | 12/2002 |
| WO | WO03039338 A2 | 5/2003 |
| WO | 2010054409 A1 | 5/2010 |
| WO | WO2010056771 A1 | 5/2010 |
| WO | 2012161880 A1 | 11/2012 |
| WO | WO2008118992 A1 | 1/2014 |
| WO | 2014072879 A2 | 5/2014 |
| WO | 2015143061 A1 | 9/2015 |
| WO | 2015183635 A1 | 12/2015 |

OTHER PUBLICATIONS

International Search Report and Written Opinion issued in PCT/US2008/058324, dated Aug. 18, 2008, 11 pages.
International Search Report and Written Opinion issued in PCT/US2012/055309, mailed Nov. 19, 2012, 13 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial International Search Report issued in PCT/US2012/0551545, mailed Dec. 20, 2012, 7 pages.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
International Preliminary Examination Report issued in PCT/US2013/060183, completed Mar. 24, 2015, 6 pages.
International Preliminary Report on Patentability issued in PCT/US2013/056211, completed Feb. 24, 2015, 5 pages.
International Preliminary Report on Patentability issued in PCT/US2013;060194, mailed Mar. 24, 2015, 6 pages.
International Search Report and Written Opinion issued in PCT/US2013/060194, mailed Jan. 29, 2014, 10 pages.
International Search Report and Written Opinion issued in PCT/US2013/056211, mailed Jan. 20, 2014.
International Search Report and Written Opinion issued in PCT/US2013/060183, mailed Jan. 27, 2014, 10 pages.
International Search Report and Written Opinion issued in PCT/US2013/060194, mailed Jan. 29, 2014.
Haverkamp, W., et. al. Coagulation of Ventricular Myocardium Using Radiofrequency Alternating Current: Bio-Physical Aspects and Experimental Findings. PACE, 12:187-195, Jan. 1989, Part II.
International Preliminary Report on Patentability issued in PCT/US2008/058324, mailed Sep. 29, 2009, 9 pages.
International Search Report and Written Opinion issued in PCT/US2013/021013, mailed Apr. 5, 2013, 14 pages.
International Search Report and Written Opinion issued in PCT/US2015/021300, mailed Jun. 9, 2015, 11 pages.
International Search Report and Written Opinion issued in PCT/US2015/055173, mailed Jan. 18, 2016, 11 pages.
International Search Report and Written Opinion issued in PCT/US2015/057242, mailed Jan. 15, 2016, 11 pages.
International Search Report and Written Opinion issued in PCTUS2015/031591, mailed Aug. 17, 2015, 11 pages.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L. A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Ring, E. R., et. al. Catheter Ablation of the Ventricular Septum with Radiofrequency Energy. American Heart Journal, 117(6):1233-1240, Jun. 1989.
Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.

* cited by examiner

MAP AND ABLATE CLOSED-LOOP COOLED ABLATION CATHETER

CROSS-REFERENCE TO RELATED APPLICATION

This application claims the benefit of Provisional Application No. 61/702,626, filed Sep. 18, 2012, which is incorporated herein by reference in its entirety.

TECHNICAL FIELD

The present disclosure generally relates to systems and methods for providing a therapy to a patient. More particularly, the present disclosure relates to a catheter for mapping and ablating tissue within the heart of the patient including mapping electrodes deposited on an exterior surface of the ablation electrode.

BACKGROUND

Atrial fibrillation is a condition in the heart causing irregular heartbeats due to generation of abnormal electrical signals. Various treatment regimens may be followed for treating arrhythmias, such as anti-arrhythmic medications and catheter ablation.

Catheter ablation is a non-surgical, minimally invasive procedure that involves killing an abnormal heart muscle responsible for heart racing. This produces a small area of dead heart muscle called a lesion. In order to make lesions and thereby treat arrhythmia, abnormal heart muscles are first targeted and mapped, such as through a mapping technique. A catheter generally includes one or more mapping electrodes configured to carry out mapping functions and a tip ablation electrode disposed at the tip portion configured to carry out the ablation function. Mapping typically involves percutaneously introducing the catheter having one or more mapping electrodes into the patient, passing the catheter through a blood vessel (e.g., the femoral vein or artery) and into an endocardial site (e.g., the atrium or ventricle of the heart) to map bioelectrical signals arising from the myocardial tissues and thereby, recognize the tissue that is the source of the arrhythmia. The tip of the ablation catheter including the tip ablation electrode can then deliver energy to the abnormal heart muscle, which disables it.

SUMMARY

Disclosed herein are embodiments of an ablation electrode including one or more mapping electrodes deposited on an exterior surface thereof at a distal end of a map and ablate catheter, as well map and ablate catheters including such deposited mapping electrodes.

In Example 1, a system for performing mapping and ablation functions includes a catheter sized and shaped for vascular access. The catheter includes an elongate body extending between a proximal end and a distal end. The catheter further includes a tip section positioned at the distal end of the body such that the tip section includes a proximal portion and a distal portion. The system also includes one or more electrode structures on an exterior surface of the tip section such that the one or more electrode structures each includes a mapping electrode at the distal portion of the tip section and a contact pad electrically coupled to the mapping electrode.

In Example 2, the system according to Example 1, wherein the tip section includes an ablation electrode configured to deliver radio frequency (RF) energy for an RF ablation procedure, and wherein the one or more electrode structures are deposited on an exterior surface of the ablation electrode.

In Example 3, the system according to either Example 1 or Example 2, wherein the one or more electrode structures further includes an insulative base layer between each of the one or more electrode structures and the ablation electrode.

In Example 4, the system according to any of Examples 1-3, wherein the catheter includes at least one inner fluid lumen, wherein the ablation electrode includes an exterior wall that defines an open interior region within the ablation electrode, and wherein the catheter system further includes a thermal mass within the open interior region and a cooling chamber in fluid communication with the at least one inner fluid lumen of the elongate body and positioned proximally to the thermal mass.

In Example 5, the system according to any of Examples 1-4, wherein the ablation electrode includes an exterior wall that defines an open interior region within the ablation electrode, wherein the exterior wall includes irrigation ports, and wherein the irrigation ports are in fluid communication with the open interior region to allow fluid to flow from the open interior region through the irrigation ports.

In Example 6, the system according to any of Examples 1-5, wherein the tip section includes a flexible balloon removably coupled to the distal end of the catheter.

In Example 7, the system according to any of Examples 1-6, and further comprising one or more mapping ring electrodes disposed on the body proximal to the one or more electrode structures.

In Example 8, the system the system according to any of Examples 1-7, wherein each of the one or more electrode structures further includes a conductive trace between the contact pad and mapping electrode, and an insulative coating layer over the conductive trace.

In Example 9, the system according to Examples 8, wherein the conductive trace has an impedance of less than 100 ohms.

In Example 10, the system according to any of Examples 1-9, wherein the one or more electrode structures are formed via physical vapor deposition.

In Example 11, a system for performing mapping and ablation functions includes a catheter sized and shaped for vascular access. The catheter includes an elongate body extending between a proximal end and a distal end and having at least one inner fluid lumen. The system further includes an ablation electrode coupled to the distal end of the catheter body, wherein the ablation electrode is configured to deliver radio frequency (RF) energy for an RF ablation procedure. The ablation electrode also includes an exterior wall that defines an open interior region within the ablation electrode. The system further includes a thermal mass within the open interior region and a cooling chamber in fluid communication with the at least one inner fluid lumen of the elongate body and positioned proximally to the thermal mass. The system further includes one or more insulative base layers on an exterior surface of the ablation electrode and one or more mapping electrodes each disposed on one of the one or more insulative base layers such that each mapping electrode can be proximate to a distal end of the ablation electrode.

In Example 12 the system according to Example 11, and further comprising one or more contact pads at a proximal end of the ablation electrode, wherein each contact pad is electrically coupled to one of the one or more mapping electrodes.

In Example 13, the system according to either Example 11 or Example 12, wherein each contact pad is connected to one of the one or more mapping electrodes via a conductive trace.

In Example 14, the system according to Example 13, and further comprising an insulative coating layer over the conductive trace.

In Example 15, the system according to any of Examples 11-14, and further comprising one or more mapping ring electrodes disposed on the body proximal to the one or more electrode structures.

In Example 16, the system according to any of Examples 11-15, wherein the mapping electrodes are formed via physical vapor deposition.

In Example 17, a system for performing mapping and ablation functions includes a radio frequency (RF) generator, a fluid reservoir and pump, a mapping signal processor, and a catheter sized and shaped for vascular access. The catheter includes an elongate body extending between a proximal end and a distal end having at least one inner fluid lumen in fluid communication with the fluid reservoir and pump. The system further includes an ablation electrode coupled to the distal end of the catheter body, and operably connected to the RF generator. The ablation electrode includes an exterior wall that defines an open interior region within the ablation electrode. The system further includes one or more insulative base layers on an exterior surface of the ablation electrode and one or more mapping electrodes operably connected to the mapping signal processor such that each mapping electrode can be disposed on one of the one or more insulative base layers. Each mapping electrode can be proximate to a distal end of the ablation electrode.

In Example 18 the system according to Example 17, and further comprising a thermal mass within the open interior region and a cooling chamber in fluid communication with the at least one inner fluid lumen of the elongate body and positioned proximally to the thermal mass.

In Example 19 the system according to either Example 17 or Example 18, and further comprising one or more contact pads at a proximal end of the ablation electrode electrically connected to the mapping signal processor, wherein each contact pad is electrically coupled to one of the one or more mapping electrodes via a conductive trace.

In Example 20, the system according to Example 19, and further comprising an insulative coating layer over each conductive trace.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
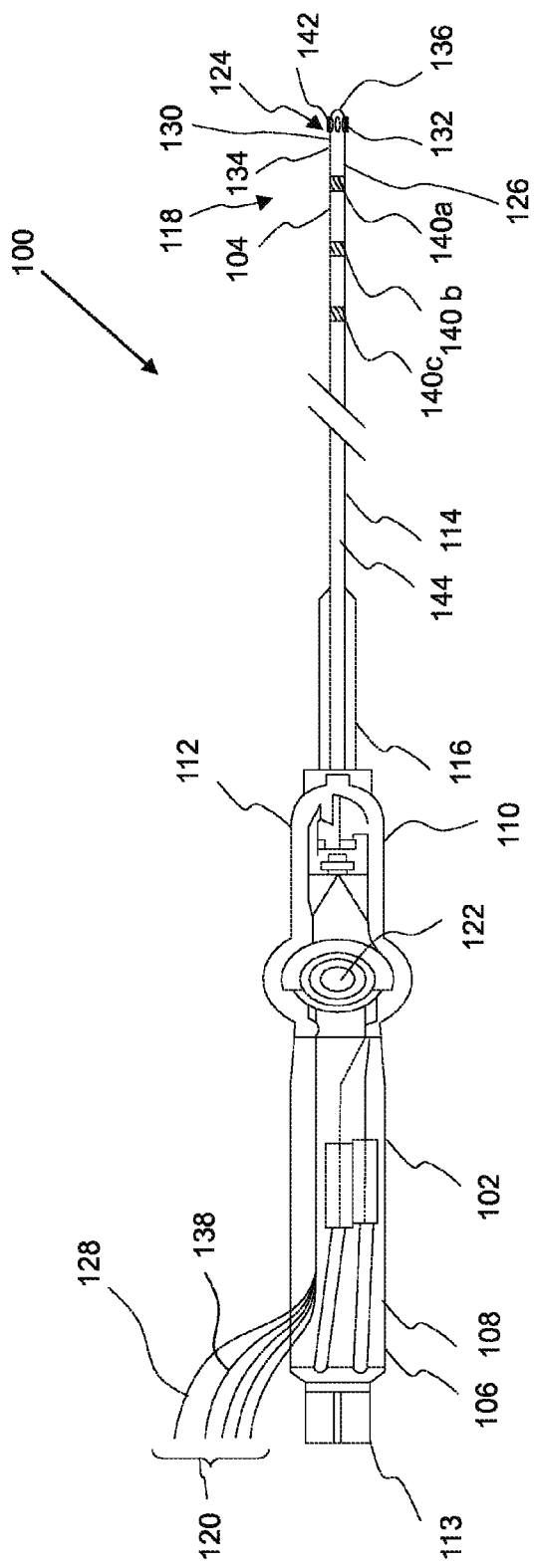
FIG. 1 is a schematic view of an embodiment of a system for performing mapping and ablation functions including a map and ablate catheter.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a front view of a system 100 for performing mapping and ablation functions. As shown, the system 100 includes a catheter 102 sized and shaped for vascular access. The catheter 102 has a distal end 104 and a proximal end 106. In one aspect, the proximal end 106 of the catheter 102 includes a handle 108 having a proximal portion 110 and a distal portion 112, and is configured to be comfortably held by a practitioner during a treatment procedure involving ablation. The handle 108 can be composed of a durable and rigid material, such as medical grade plastic, and ergonomically molded to allow the physician to more easily manipulate the catheter 102. The handle 108 can incorporate a plurality of conduits, conductors, and wires to facilitate control of the catheter 102 and/or mating of the catheter 102 with a source of fluid, a source of ablative energy, a source of mapping, temperature display, sensors, and/or control software/hardware. The handle 108 further includes a connection port 113 through which ablative energy source and a mapping energy source can be operably coupled.

The catheter 102 can include an elongate body 114 having a proximal end 116 and a distal end 118. The body houses electrical conductors/cable assembly (e.g., wires) 120 for transmitting sensed signals and/or ablation energy. The elongate body 114 is preferably about 1.67 mm to 3 mm in diameter, and between 800 mm to 1500 mm in length. The elongate body 114 preferably has a circular cross-sectional geometry. However, other cross-sectional shapes, such as elliptical, rectangular, triangular, and various other shapes, can be provided. In some embodiments, the elongate body 114 can be preformed of an inert, resilient plastic material that retains its shape and does not soften significantly at body temperature; for example, Pebax®, polyethylene, or Hytrel® (polyester). Alternatively, the elongate body 114 can be made of a variety of materials, including, but not limited to, metals and polymers. The elongate body 114 is preferably flexible so that it is capable of winding through a tortuous path that leads to a target site, i.e., an area within the heart. Alternatively, the elongate body 114 can be semi-rigid, i.e., by being made of a stiff material, or by being reinforced with a coating or coil, to limit the amount of flexing.

In some embodiments, the movement of the distal end 118 of the elongate body 114 (such as to wind through the tortuous path that leads to a target site) can be controlled by a control mechanism 122 included within the handle 120. The system 100 can include an articulating section of the elongate body 114 (e.g., near the distal end 118) that is controlled via the control mechanism 122. In some embodiments, the distal end 118 of the elongate body 114 can be deflected or bent. The articulation section of the body can facilitate insertion of the catheter 102 through a body lumen (e.g., vasculature) and/or placement of electrodes at a target tissue location. The articulation section can provide one or more degrees of freedom and permit up/down and/or left/right articulation. One skilled in the art will understand that the control mechanism 122 and the articulating section of the catheter 102 can include a variety of features associated with conventional articulating catheters.

The distal end 104 of the catheter 102 includes a tip section 124 positioned at the distal end 118 of the elongate body 114. The tip section 124 includes a proximal portion 134 and a distal portion 136. In some embodiments, the tip section 124 is formed from a conductive material. For example, in some embodiments the tip section 124 is comprised of a platinum-iridium alloy. In one exemplary embodiment, the platinum iridium top section 124 comprises an alloy with approximately 90% platinum and 10% iridium. This conductive material is used to conduct radio frequency (RF) energy used to form lesions during the ablation procedure. The ablation electrode 126 can have any suitable length, for example, in the range between 4 mm and 10 mm. The ablation electrode 126 can be composed of a solid, electrically conductive material, such as platinum, gold, or stainless steel. The ablation electrode 126 can be configured to deliver ablation energy to the myocardial tissues that are the source of arrhythmia, thereby destroying them or a portion thereof through heat. In an embodiment, the ablation electrode 126 can be electrically coupled to an RF generator, which will be discussed in further detail with regards to FIG. 2, so that ablation energy can be conveyed from the RF generator to the ablation electrode 126 to form localized lesions in the myocardial tissues. In an embodiment, an RF wire 128 can be electrically connected to the ablation electrode 126 using suitable means, such as soldering or welding. The RF wire 128 can pass through a lumen 144 extending through the elongate body 114 of the catheter 102, where it is further electrically coupled to the cable assembly 120 located within the handle 108 and to the RF generator exteriorly coupled to the catheter system 100.

The system 100 includes one or more electrode structures 142 on an exterior surface 130 of the tip section 124. The electrode structures 142 each include a mapping electrode 132 at the distal portion 136 of the tip section 124. The mapping electrode 132 is deposited on the tissue ablation electrode 126, and in particular, is deposited on an exterior surface 130 of the ablation electrode 126. This can allow the localized intracardial electrical activity to be measured in real time at the point of RF energy delivery from the ablation electrode 126 thereby allowing the physician to ascertain lesion formation by measuring the electrical activity of the tissue in contact with the tip ablation electrode 126 (e.g., the lack of electrical activity indicates ablated tissue, whereas the presence of electrical activity indicates live tissue). In some embodiments, the mapping electrodes 132 are deposited on the exterior surface 130 of the ablation electrode 126. In some embodiments, the one or more electrode structures 142 are deposited via physical vapor deposition (PVD). The physical vapor deposition may be used for the deposition of the electrodes formed of a metal. In alternative embodiments, other deposition techniques may be used for electrode deposition on the exterior surface 130 of the ablation electrode 126, such as sputtering.

In some embodiments, the electrode structures 142 each includes a contact pad that is electrically coupled to the mapping electrode 132. The contact pad can be configured to provide connection of the mapping electrode 132 with the cable assembly 120, thereby allowing the mapping electrode 132 to form electrical connection with the electrical circuitry of the catheter 102. In some embodiments, the mapping electrode 132 are electrically coupled to a mapping signal processor, which will be discussed in further detail with regards to FIG. 2, so that electrical events in myocardial tissue can be sensed for the generation of electrograms, monophasic action potentials (MAPs), isochronal electrical activity maps, and the like. In some embodiments, the signal wires 138 are respectively connected to the mapping electrodes 132 using suitable means such as soldering or welding. The signal wires 138 can pass through a lumen 144 extending through the elongate body 114 of the catheter 102, where it is electrically coupled to the cable assembly 120 located within the handle 108 and then to the mapping microprocessor.

The system 100 may also include one or more mapping ring electrodes 140. The mapping ring electrodes 140 can be configured to map the bioelectrical signals arising from the myocardial tissues and thereby recognize the tissues that are the source of arrhythmia. The mapping ring electrodes 140 can include a distal mapping ring electrode 140a, a medial mapping ring electrode 140b, and a proximal mapping ring electrode 140c. The mapping ring electrodes 140a, 140b, and 140c as well as the ablation electrode 126 are capable of forming a bipolar mapping electrode pairs. For example, the ablation electrode 126 and distal mapping ring electrode 140a can be configured as a first bipolar mapping electrode pair, the distal mapping ring electrode 140a and the medial mapping ring electrode 140b can be configured as a second bipolar mapping electrode pair, the medial mapping ring electrode 140b and the proximal mapping ring electrode 140c can be configured as a third bipolar mapping electrode pair, or any combination thereof. Like the mapping electrodes 132, the mapping ring electrodes 140a-140c are also electrically coupled to the mapping signal processor via the signal wires 138 to map electrical events in the myocardial tissues.

Figure 2:
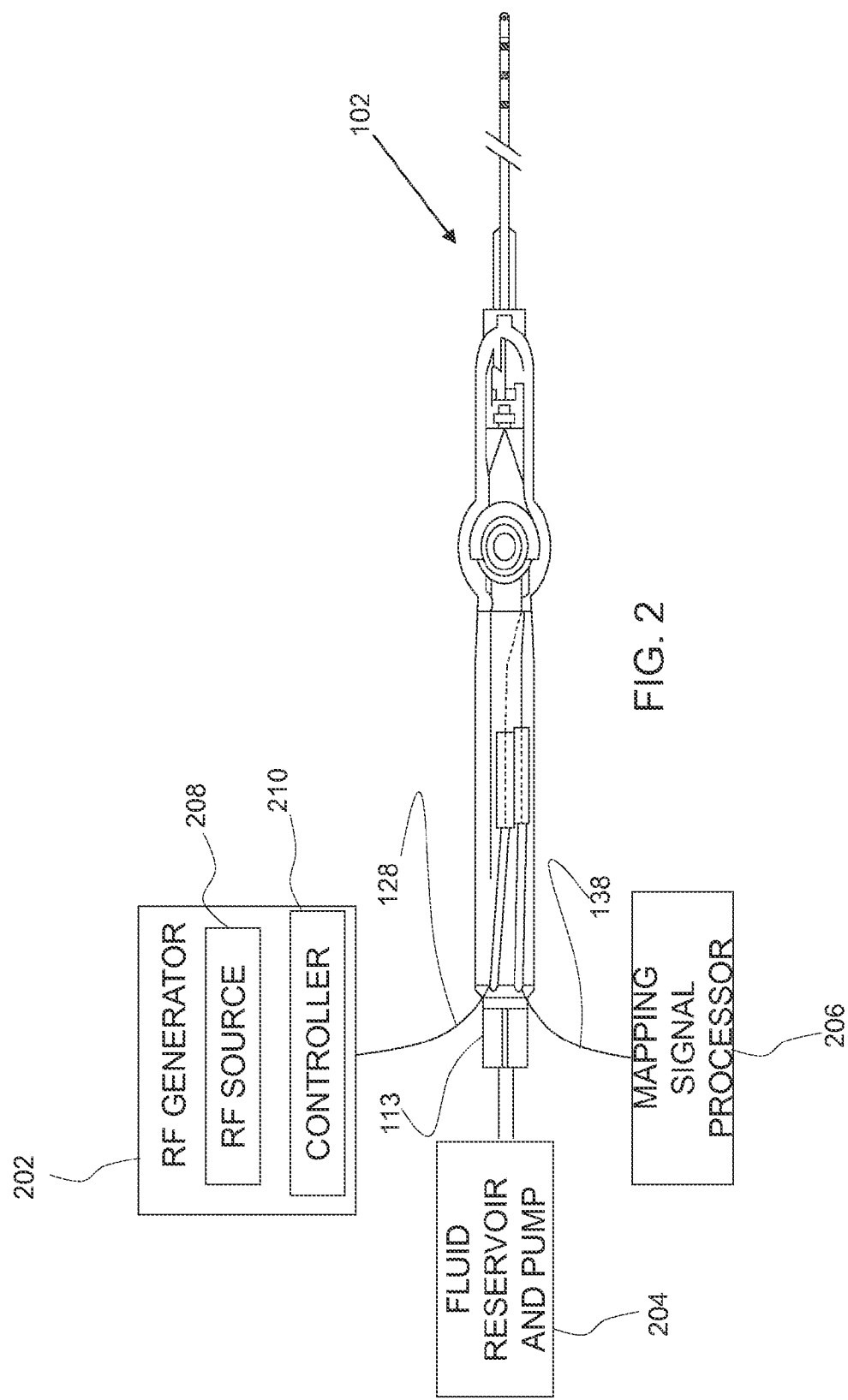
FIG. 2 is a schematic view of another embodiment of a system for performing mapping and ablation functions including a map and ablate catheter.

FIG. 2 illustrates an embodiment of the mapping and ablation system 100 including cooling, ablation, and mapping system components and a closed-irrigated catheter 102. The catheter 102 can be configured to be introduced through the vasculature of the patient, and into one of the chambers of the heart, where it can be used to map and ablate myocardial tissue. The system 100 also comprises a radio frequency (RF) generator 202, a fluid reservoir and pump 204, a mapping signal processor 206, coupled to the catheter 102 via a cable assembly or through connection port 113. In an embodiment, the radio frequency (RF) generator 202, and the mapping signal processor 206 can be connected to the catheter 102 through the RF wire 128 and the signal wires 138 of the cable assembly 120. In an embodiment, the fluid reservoir and pump 204 can be connected to the catheter 102 through the connection port 113.

Although the radio frequency (RF) generator 202, the fluid reservoir and the pump 204, and the mapping signal processor 206 are shown as discrete components, they can alternatively be incorporated into a single integrated device.

In some embodiments, the ablation electrode 126 coupled to the distal end 118 of the catheter body 114 can be operably connected to the RF generator 202. The RF generator 202 can be used to generate the energy for the ablation procedure. The RF generator 202 includes a source 208 for the RF energy and a controller 210 for controlling the timing and the level of the RF energy delivered through the tip 204. The illustrated system 100 also includes the fluid reservoir and pump 204 for pumping cooling fluid, such as a saline, through an inner fluid lumen of the catheter 102 (which will be discussed in greater detailed below) to the tip portion 124.

The mapping signal processor 206 can be operably coupled to the one or more electrodes similar to the mapping electrode 132. The mapping signal processor 206 can be configured to detect, process, and record electrical signals within the heart via the one or more electrodes of the catheter 102. Based on the electrical signals sensed by the one or more electrodes, the physician can identify the specific target tissue sites within the heart, and ensure that the arrhythmia causing substrates have been electrically isolated by the ablative treatment. Based on the detected electrical signals, the mapping signal processor 206 outputs electrocardiograms (ECGs) to a display (not shown), which can be analyzed by the physician to determine the existence and/or location of arrhythmia substrates within the heart and/or determine the location of the catheter 102 within the heart. In some embodiments, the mapping signal processor 206 can generate an isochronal map of the detected electrical activity and output the map to the display for analysis by the physician.

Figure 3:
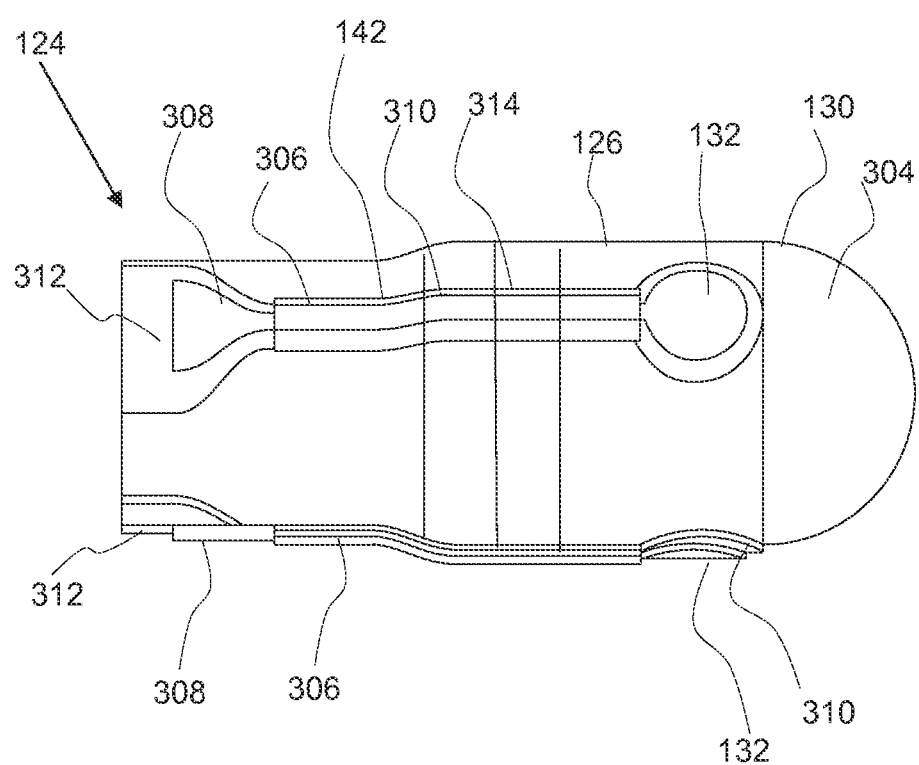
FIG. 3 is a side view of an embodiment of a tip section of a map and ablate catheter including an ablation electrode with one or more electrode structures deposited thereon.

FIG. 3 is a side view of the tip section 124 including the ablation electrode 126 with the one or more electrode structures 142 deposited thereon. As shown in FIG. 3, the tip section 124 comprises the ablation electrode 126 configured to deliver radio frequency (RF) energy for the RF ablation procedure and the electrode structures 142. The electrode structures 142 each include the mapping electrode 132. The mapping electrodes 132 can be disposed on the tissue ablation electrode tip 304, and in particular, are deposited on the exterior surface 130 of the tissue ablation electrode tip 304. This allows the localized intracardial electrical activity to be measured in real time at the point of energy delivery from the ablation electrode 126. In addition, the mapping electrodes 132 do not sense far field electrical potentials that would normally be associated with bipolar measurements taken between the tissue ablation electrode 126 and the mapping ring electrodes 140a, 140b, 140c, due to their relatively small size and spacing between each of the electrode structures 142. Instead, the mapping electrodes 132 measure the highly localized electrical activity at the point of contact between the ablation electrode 126 and the endocardial tissue. Thus, the arrangement of the mapping electrodes 132 substantially enhances the mapping resolution of the catheter 102. The high resolution inherent in the arrangement of the mapping electrodes 132 allows a user to measure complex localized electrical activity more precisely, resulting in a powerful tool for diagnosing electrocardiogram (ECG) activity, for example, the high frequency potentials that are encountered around pulmonary veins or the fractioned ECGs associated with atrial fibrillation triggers. The arrangement of the mapping electrodes 132 can also allow generation of high density electrical activity maps such as electrical activity isochronal maps, which may be combined with anatomical maps, to create electro-anatomical maps. In addition, detection of tissue contact and tissue characterization, including lesion formation assessment, can be made more accurate due to the elimination or minimization of the detected far field electrical activity.

The mapping electrodes 132 can be small, independent diagnostic sensing electrodes deposited on the exterior surface 130 of the tip 304 of the RF ablation catheter 102. Each mapping electrode 132 can be composed of an electrically conductive material, such as platinum, gold, or stainless steel. In some embodiments, the mapping electrodes 132 are comprised of a silver/silver chloride to maximize the coupling between the mapping electrode 132 and blood, thereby optimizing signal fidelity. In some embodiments, the electrode structures 142 are formed via physical vapor deposition (PVD) or other suitable methods for deposing the electrodes onto the exterior surface 130.

The mapping electrodes 132 can be disposed on the ablation electrode 126 in any one of a variety of different patterns. In an example, as shown in FIG. 3, the mapping electrodes 132 are circumferentially disposed about the cylindrical-shaped region of the ablation electrode 126 at 120° intervals so that they face radially outward in different directions.

In some embodiments, each of the electrode structures 142 further includes a conductive trace 306 electrically coupled to the mapping electrode 132 and a contact pad 308 electrically connected to the conductive trace 306. In some embodiments, the contact pads 308 are disposed at a proximal portion of the tip 304. The contact pad 308 may be configured for electrical connection to a diagnostic device such as the mapping processor 206. In an embodiment, the conductive trace 306 can be offset either along the longitudinal or lateral axes of the catheter system 102 from the mapping electrode 132 so long as some portion of the conductive trace 306 remains in contact with the mapping electrode 132. Accordingly, the lateral and longitudinal cross-sections of both the mapping electrode 132 and the conductive trace 306 may vary similar to the variation in the depth or thickness of the conductive trace 306 and mapping electrode 132. In some embodiments, the conductive traces 306 have an impedance of less than 100 ohms.

In some embodiments, the catheter 102 includes a plurality of internal conductors each coupled to one of the contact pads 308. Thus, each of the mapping electrodes 132 can be electrically connected to other semiconductor devices, electronic components on the substrate, or components that are external to the catheter 102 such as the mapping processor.

In some embodiments, the electrodes 126, 132, and/or 140, the conductive trace 306, and contact pad 308 can be made from the same conductive materials. In some embodiments, the electrodes 126, 132, and/or 140, conductive trace 306, and contact pad 308 can be made of different conductive materials. For example, the contact pads 308 can be formed of a material such as gold (Au), platinum (Pt), palladium (Pd), ruthenium (Ru), rhodium (Rh), iridium (Ir), carbon (C), or other material that resists oxidation. The conductive traces 306 can be formed of any suitable conductive material, such as Au, Pt, or copper (Cu). The electrodes 126, 132, and/or 140, conductive trace 306, or contact pad 308 may be comprised of any suitable material including, for example, Pt, Au, Pd, Ru, Rh, Ir, silver (Ag), C, and their alloys or oxides. Conducting polymers, such as polypyrrole (PPy), polyaniline (PANi), polythiophene, poly(3,4-ethylenedioxythiophene) (PEDOT) or their derivatives may also be employed for the conductive elements of the catheter 102.

The electrode structures 142 may further include a multi-layer dielectric material 310 such that the multi-layer dielectric material 310 includes an insulative base layer 312 and/or an insulative coating layer 314. The multi-layer dielectric material 310 acts as a dielectric barrier between the ablation electrode 126 and the electrode structures 142 resisting the conductance of the RF energy from the ablation electrode 126 to the electrode structures 142. For this purpose, the system 100 includes the insulative base layers 312 between each of the one or more electrode structures 142 and the ablation electrode 126.

The insulative base layer 312 can be composed of a suitable electrically and thermally insulative material, such as a high temperature thermoset plastic with high dielectric properties, e.g., polyimide or plastics from the phenolic group, such as Bakelite® or Ultem® plastics. The electrically insulative material of the insulative base layer 312 makes the mapping electrode 132 electrically insulated from the ablation electrode 126, and thus, from each other, so that each of the mapping electrode 132 can provide independent mapping channels. The thermal insulative material of the insulative base layer 312 makes the mapping electrode 132 thermally insulated from the ablation electrode 126 to prevent saturation of the mapping channels that would otherwise cause interference from the heat generated during a radio frequency (RF) ablation procedure. The insulative base layer 310 can be formed on the exterior surface 130 of the ablation electrode 126 in a manner such that the mapping electrodes 132 can be each disposed on the insulative base layers 312 such that each of the mapping electrode 132 can be proximate to the ablation electrode 126. The insulative base layer 312 can be further coated with an insulative coating layer 314 such that the insulative coating layer 314 is provided over each of the conductive trace 306. The insulative coating layer 314 electrically isolates the conductive trace from surrounding structures.

Figure 4:
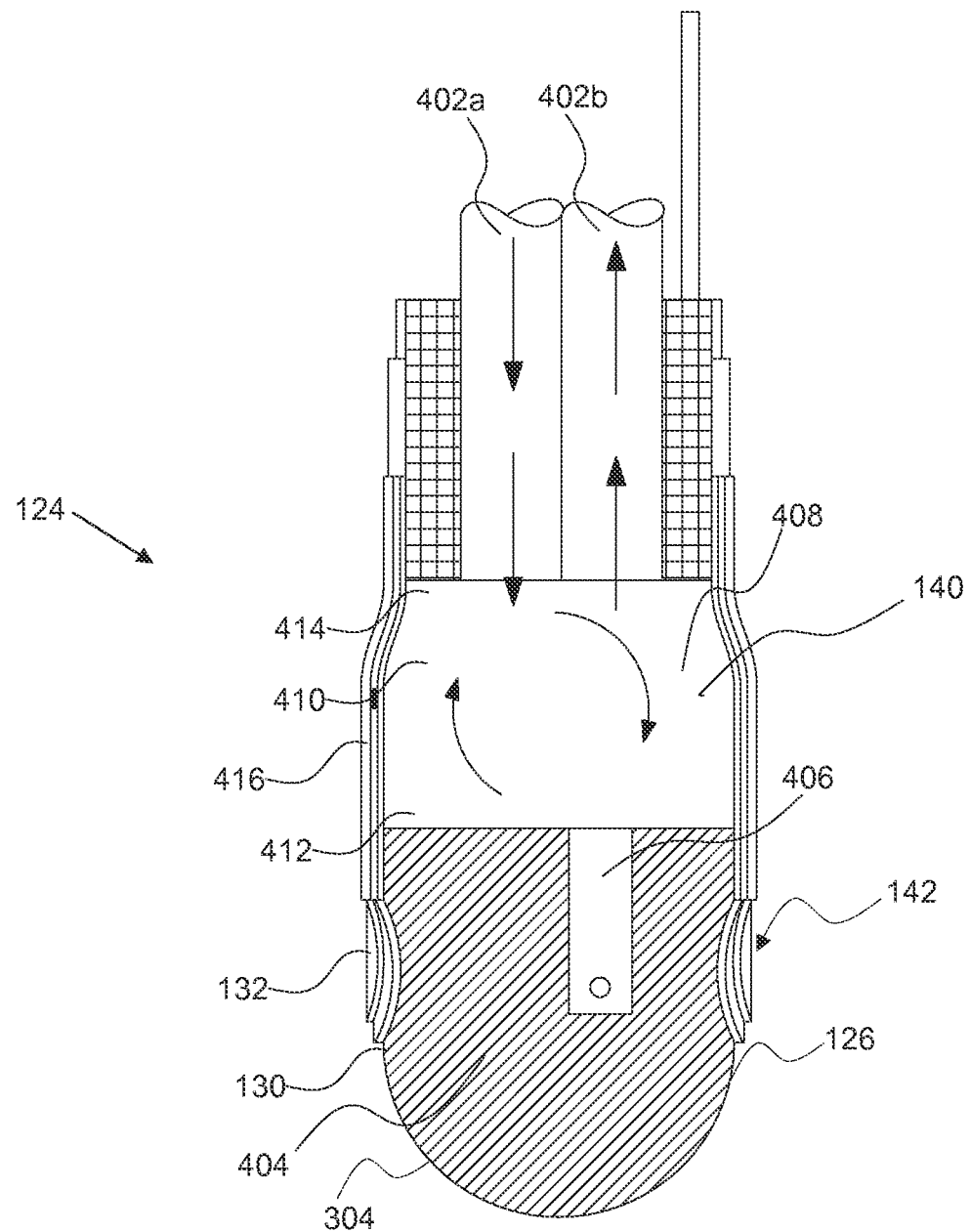
FIG. 4 is a cross-sectional view of an embodiment of the tip section of the map and ablate catheter including deposited mapping electrode structures and a closed-loop cooling system.

FIG. 4 is a cross-sectional view of an embodiment of the tip section 124 of the map and ablate catheter including deposited electrode structures 142 and a closed-loop cooling system. The tip section 124 includes at least one inner fluid lumen 402 in fluid communication with the fluid reservoir and pump 204 (shown in FIG. 2). The ablation electrode 126 is configured to deliver RF energy for the RF ablation procedure. Generally, the tip section 124 on which the ablation electrode 126 is formed can be a hollow tip section 124 and can include an open interior region 410 defined by the exterior wall 130 of the tip section 124.

In some embodiments, the tip section 124 includes a thermal mass 404. The thermal mass 404 comprises a material having a high thermal conductivity. A temperature sensor 406 can be positioned at least partially within the thermal mass 404. In an embodiment, the thermal mass 404 substantially extends across the full width of the tip 124.

The tip section 124 further includes a cooling chamber 408 in fluid communication with the inner fluid lumens 402 of the elongate body 114 and positioned proximally to the thermal mass 404. The cooling chamber 408 substantially extends across an entire width of the tip 124 between the exterior walls similar to the exterior wall 130 of the tip 304. The cooling chamber 408 can be defined in the form of a cavity near the proximate end of the tip 124 that is bounded at its distal end 412 by the thermal mass 404 and is bounded at its proximal end 414 by a portion of the tip section 124 and/or by a portion of the elongate catheter body 114.

In the illustrated embodiment, the cooling chamber 408 is positioned proximal to at least a portion of the thermal mass 404 and/or adjacent to the proximal portion 110 of the tip section 124. As ablation energy moves through the tip section 124, areas of increased current density can develop and result in localized hotspots. The system 100, described herein, can reduce the effect of proximal hotspots through the use of the cooling chamber 408 in fluid communication with the fluid lumen 402 of the elongate body 114. As shown in FIG. 4, a first fluid lumen 402a and a second fluid lumen 402b are in fluid communication with the tip 124. The first lumen 402a can deliver a cooling fluid into, for example, the cooling chamber 408. At least a portion of the cooling fluid can then continue on a path as shown along the arrow directions, and as illustrated in FIG. 4. The tip 124 includes the second fluid lumen 402b for removing cooling fluid after the cooling fluid has absorbed heat within the cooling chamber 408. The second fluid lumen 402b can return the heated fluid through the catheter body 114 for egress from the system 100 to a proximal location, such as the fluid reservoir and pump 204 for cooling and/or recirculation. As a result, heat can be removed from the tip 124 through the path (as shown along the arrow directions) of the cooling fluid.

The tip section 124 includes one or more insulative base layers 416 on the exterior surface 130 of the ablation electrode 126 and one or more mapping electrodes similar to the mapping electrode 132 each disposed on one of insulative base layers 416. The electrically insulative material of the insulative base layer 416 makes the mapping electrode 132 electrically insulated from the ablation electrode 126 and from each other so that each of the mapping electrodes 132 can provide independent mapping channels.

Figure 5:
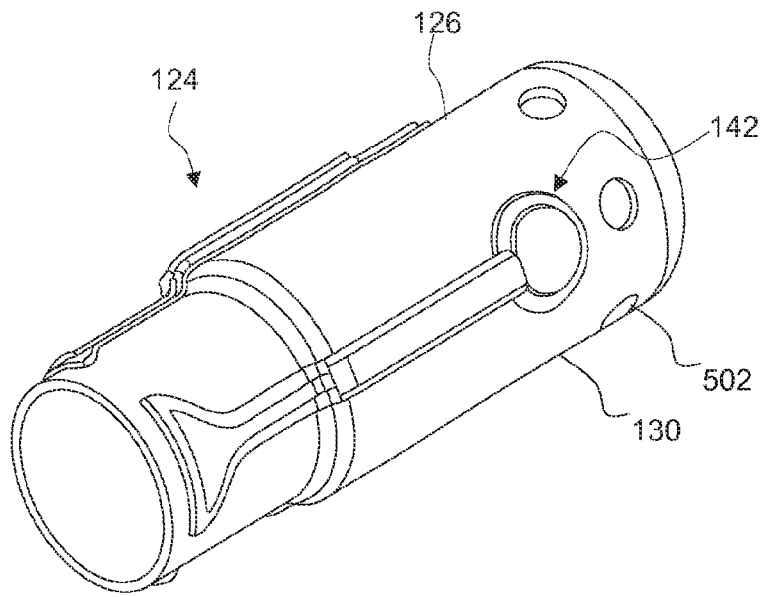
FIG. 5 is a perspective view of an embodiment of an open irrigated tip section of a map and ablate catheter including deposited mapping electrode structures.
Figure 6:
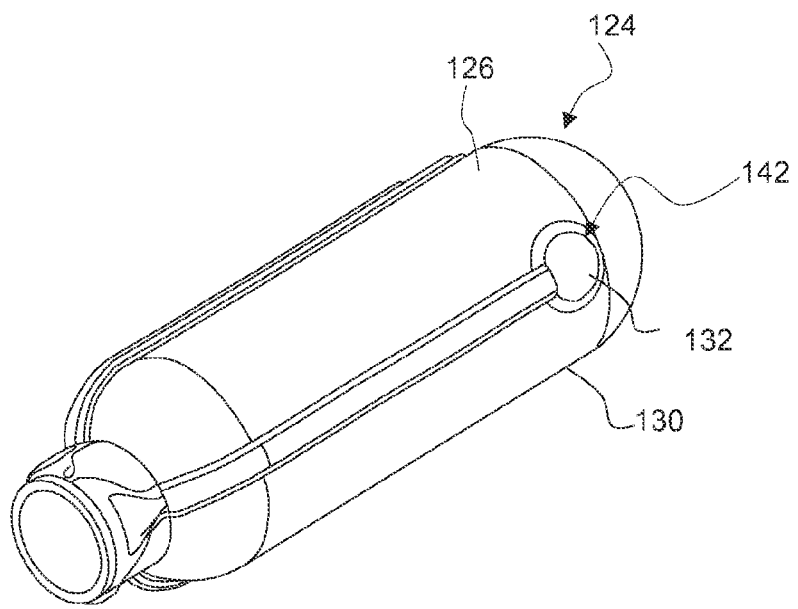
FIG. 6 is a perspective view of an embodiment of a non-irrigated tip section of a map and ablate catheter including deposited mapping electrode structures.

FIGS. 5 and 6 are perspective views of an open irrigated tip and a non-irrigated tip, respectively, including the deposited one or more electrode structures 142. The catheter 102 as described in conjunction with the present invention can be a hybrid catheter 102 as it can be used simultaneously for both localized mapping and ablation functions. The catheter 102 can be configured to provide localized, high resolution ECG signals during ablation. The localized mapping enables the mapping to be precise. As shown in FIG. 5, the catheter 102 has an open-irrigated catheter design. The hollow tip section 124 on which the ablation electrode 126 are formed includes the open interior region 410 defined by the exterior wall 130 of the tip section 124. The exterior wall 130 further includes a plurality of irrigation ports 502. The irrigation ports 502 are in fluid communication with the open interior region 410 to allow fluid to flow from the open interior region 410 through the irrigation ports 502. A cooling fluid, such as a saline fluid, is delivered from a fluid reservoir and pump 202 (shown in FIG. 2) through the catheter 102 to the tip section 124, where the fluid exits through irrigation ports 502 to cool the ablation electrode 126 and surrounding tissue. Clinical benefits of such catheter 102 can include, but are not limited to, controlling the temperature and reducing coagulum formation on the tip section 124 of the catheter 102, preventing impedance rise of tissue in contact with the tip section 124, and maximizing potential energy transfer to the tissue. Additionally, the localized intra cardiac electrical activity can be recorded in real time or near-real time right at the point of energy delivery. However, the hybrid catheter design of the present disclosure can also have a non-irrigated design as shown in FIG. 6 n a non-irrigated tip catheter 102.

Figure 7:
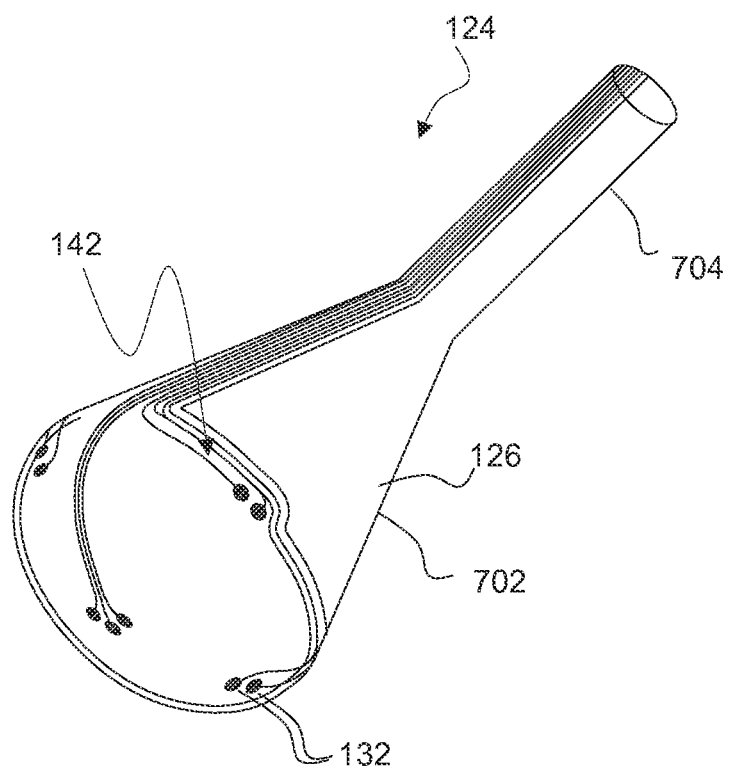
FIG. 7 is a perspective view of an embodiment of a mapping balloon including mapping electrodes deposited thereon.

FIG. 7 illustrates a perspective view of a mapping balloon 702 for the purpose of mapping anatomical features and tissue. In an embodiment, the tip section 124 comprises the mapping balloon 702 which is removably coupled to the distal end 104 of the catheter 102. The balloon 702 can be mounted circumferentially on the distal end 118 of the elongate body 114 of the catheter 102. The balloon 702 can be elastic, and may be comprised of polyethylene cross-linked latex, although other biocompatible elastomer materials can be used. The balloon 702 at its surface can include an electrode diagnostic array feature. The electrode diagnostic array feature can include any or all of the electrodes such as one or more electrode structures 142, ablation electrode 126, and the mapping ring electrodes 140 for the purpose of ablating and mapping tissues. In some embodiments, the electrode array diagnostic array feature can include one or more electrode structures 142 each containing a mapping electrode 132 configured for picking up bioelectrical signals from the walls of blood vessels. The mapping electrodes 132 sense electrical potentials within the heart for the purpose of locating cardiac tissue containing abnormal electrical pathways. The balloon 702 can have a structure that can be easily adaptable to any one of the cardiac chambers and which can be used in the right or left ventricles of the heart without resorting to a ventriculotomy for mapping and/or ablating tissues of the heart. A proximal end 704 of the balloon 702 can be attached at the distal end 104 of the catheter 102 and can be constructed for insertion into a blood vessel. The balloon 702 can be mounted on the distal end 104 of the catheter 102 and a heating device (not shown) can also be mounted on the distal end 104 of the catheter 102 such that the heating device can be arranged for heating tissue in contact with the balloon 702 while the balloon 702 is inflated. In some embodiments, the catheter body 114 and the balloon 702 are sized and constructed to permit the distal end 118 of the catheter body 114 to be inserted into an atrium or ventricle of a heart while the balloon 702 is in a deflated configuration. The distal end 104 of the catheter 102 can be positioned within the atrium or ventricle and adjacent to a wall of the atrium or ventricle. The balloon 702 can then be inflated with fluid while the balloon 702 can be within the atrium or ventricle, for example to engage in direct contact with a wall of the atrium or ventricle. A tissue surrounding the balloon 702 can be heated through use of the heating device while the balloon 702 is inflated.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A system comprising:
    a catheter sized and shaped for vascular access and including an elongate body extending between a proximal end and a distal end;
    a tip section including an ablation electrode configured to deliver radio frequency (RF) energy for an RF ablation procedure and positioned at the distal end of the body, the tip section including a proximal portion and a distal portion; and
    one or more electrode structures on an exterior surface of the ablation electrode, the one or more electrode structures each including a mapping electrode at the distal portion of the tip section and a contact pad electrically coupled to the mapping electrode.

2. The system of claim 1, wherein the one or more electrode structures further includes an insulative base layer between each of the one or more electrode structures and the ablation electrode.

3. The system of claim 1, wherein the catheter includes at least one inner fluid lumen, wherein the ablation electrode comprises an exterior wall that defines an open interior region within the ablation electrode, and wherein the system further comprises:
    a thermal mass within the open interior region; and
    a cooling chamber in fluid communication with the at least one inner fluid lumen of the elongate body and positioned proximally to the thermal mass.

4. The system of claim 1, wherein the ablation electrode comprises an exterior wall that defines an open interior region within the ablation electrode, wherein the exterior wall includes irrigation ports, and wherein the irrigation ports are in fluid communication with the open interior region to allow fluid to flow from the open interior region through the irrigation ports.

5. The system of claim 1, and further comprising one or more mapping ring electrodes disposed on the body proximal to the one or more electrode structures.

6. The system of claim 1, wherein each of the one or more electrode structures further comprises:
    a conductive trace between the contact pad and mapping electrode; and
    an insulative coating layer over the conductive trace.

7. The system of claim 6, wherein the conductive trace has an impedance of less than 100 ohms.

8. The system of claim 1, wherein the one or more electrode structures are formed via physical vapor deposition.

9. A system for performing mapping and ablation functions, the system comprising:
    a catheter sized and shaped for vascular access and including an elongate body extending between a proximal end and a distal end and having at least one inner fluid lumen;
    an ablation electrode coupled to the distal end of the catheter body, the ablation electrode configured to deliver radio frequency (RF) energy for an RF ablation procedure, the ablation electrode including an exterior wall that defines an open interior region within the ablation electrode;
    a thermal mass within the open interior region;
    a cooling chamber in fluid communication with the at least one inner fluid lumen of the elongate body and positioned proximally to the thermal mass;
    one or more insulative base layers on an exterior surface of the ablation electrode; and
    one or more mapping electrodes each disposed on one of the one or more insulative base layers, each mapping electrode proximate a distal end of the ablation electrode.

10. The system of claim 9, and further comprising:
    one or more contact pads at a proximal end of the ablation electrode, wherein each contact pad is electrically coupled to one of the one or more mapping electrodes.

11. The system of claim 10, wherein each contact pad is connected to one of the one or more mapping electrodes via a conductive trace.

12. The system of claim 11, and further comprising an insulative coating layer over the conductive trace.

13. The system of claim 9, and further comprising one or more mapping ring electrodes disposed on the body proximal to the one or more mapping electrodes.

14. The system of claim 9, wherein the mapping electrodes are formed via physical vapor deposition.

15. A system for performing mapping and ablation functions, the system comprising:
    a radio frequency (RF) generator;
    a fluid reservoir and pump;
    a mapping signal processor;
    a catheter sized and shaped for vascular access and including an elongate body extending between a proximal end and a distal end and having at least one inner fluid lumen in fluid communication with the fluid reservoir and pump;
    an ablation electrode coupled to the distal end of the catheter body, the ablation electrode operably connected to the RF generator, the ablation electrode including an exterior wall that defines an open interior region within the ablation electrode;
    one or more insulative base layers on an exterior surface of the ablation electrode; and
    one or more mapping electrodes operably connected to the mapping signal processor, each mapping electrode disposed on one of the one or more insulative base layers, each mapping electrode proximate a distal end of the ablation electrode.

16. The system of claim 15, and further comprising:
a thermal mass within the open interior region; and
a cooling chamber in fluid communication with the at least one inner fluid lumen of the elongate body and positioned proximally to the thermal mass.

17. The system of claim 15, and further comprising:
one or more contact pads at a proximal end of the ablation electrode electrically connected to the mapping signal processor, wherein each contact pad is electrically coupled to one of the one or more mapping electrodes via a conductive trace.

18. The system of claim 17, and further comprising:
an insulative coating layer over each conductive trace.

* * * * *